US012327627B2

(12) United States Patent
Grbic (10) Patent No.: US 12,327,627 B2
(45) Date of Patent: Jun. 10, 2025

(54) ARTIFICIAL INTELLIGENCE SUPPORTED READING BY REDACTING OF A NORMAL AREA IN A MEDICAL IMAGE

(71) Applicant: Siemens Healthineers AG, Forchheim (DE)

(72) Inventor: Sasa Grbic, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 376 days.

(21) Appl. No.: 17/822,548

(22) Filed: Aug. 26, 2022

(65) Prior Publication Data

US 2024/0071604 A1    Feb. 29, 2024

(51) Int. Cl.
*G16H 30/40*     (2018.01)
*G06T 7/00*      (2017.01)
*G06T 7/11*      (2017.01)

(52) U.S. Cl.
CPC .......... *G16H 30/40* (2018.01); *G06T 7/0012* (2013.01); *G06T 7/11* (2017.01); *G06T 2207/20081* (2013.01)

(58) Field of Classification Search
CPC ...... G16H 30/40; G16H 50/20; G06T 7/0012; G06T 7/11; G06T 2207/20081; G06T 2200/24; G06T 2207/10072; G06T 2207/30004; G06V 10/454; G06V 10/82; G06V 2201/03; G06V 10/44; G06V 10/764
USPC ....................................................... 382/128
See application file for complete search history.

(56) References Cited

U.S. PATENT DOCUMENTS

| | | | |
|---|---|---|---|
| 10,499,857 B1 * | 12/2019 | Nguyen | G06N 3/045 |
| 11,227,683 B2 * | 1/2022 | Morard | G06T 7/0014 |
| 11,848,105 B2 * | 12/2023 | Rao | A61B 5/055 |
| 2012/0323118 A1 | 12/2012 | Menon Gopalakrishna et al. | |
| 2016/0203264 A1 * | 7/2016 | Danner | H04N 1/38 382/128 |
| 2019/0197684 A1 | 6/2019 | Kamoda et al. | |
| 2020/0027561 A1 * | 1/2020 | Rao | G06V 10/454 |
| 2020/0185084 A1 * | 6/2020 | Syeda-Mahmood | G06V 10/7515 |
| 2020/0288963 A1 * | 9/2020 | Lin | G16H 80/00 |
| 2021/0216822 A1 * | 7/2021 | Paik | G16H 15/00 |
| 2021/0264212 A1 * | 8/2021 | Paik | G06N 3/08 |
| 2021/0383174 A1 | 12/2021 | Hölzer et al. | |

OTHER PUBLICATIONS

Ghesu, Florin-Cristian, et al. "Multi-scale deep reinforcement learning for real-time 3D-landmark detection in CT scans." IEEE transactions on pattern analysis and machine intelligence 41.1 (2017): 176-189.
Yang, Dong, et al. "Automatic liver segmentation using an adversarial image-to-image network." International Conference on Medical Image Computing and Computer-Assisted Intervention. Springer, Cham, 2017.
(Continued)

*Primary Examiner* — Neil R McLean (57) ABSTRACT

For supporting reading for radiologists, artificial intelligence (AI) identifies normal anatomy or parts of the patient represented in a medical image. Those parts are then altered, such as redacted, to indicate that no review of that part is needed. The reading presents medical images for review with one or more parts identified as not needing review (e.g., by being missing through redaction).

19 Claims, 2 Drawing Sheets

(56) References Cited

OTHER PUBLICATIONS

Gundel, Sebastian, et al. "Robust classification from noisy labels: Integrating additional knowledge for chest radiography abnormality assessment." Medical Image Analysis 72 (2021): 102087.
Ghesu, Florin C., et al. "Quantifying and leveraging predictive uncertainty for medical image assessment." Medical Image Analysis 68 (2021): 101855.
Extended European Search Report (EESR) mailed Jan. 15, 2024 in corresponding European Patent Application No. 23192926.6.

* cited by examiner

ARTIFICIAL INTELLIGENCE SUPPORTED READING BY REDACTING OF A NORMAL AREA IN A MEDICAL IMAGE

BACKGROUND

The present embodiments relate to use of artificial intelligence (AI) in healthcare. Reading and reporting of medical images is done primarily by radiologists. The radiologist examines the 2D (e.g., X-Ray) or 3D (e.g., computed tomography (CT) or magnetic resonance imaging (MRI)) image and reports any abnormalities seen in the entire medical image. Even though a specific indication is often available for the scan (e.g., patient suspected with lung cancer, patient with pulmonary embolism suspicion, . . . ), the radiologist still reviews for any finding that goes beyond the clinical question required for the scan. This is a tedious task and usually involves multiple examinations of the same region, going through a pre-defined visual checklist. For example, for a Chest CT, the list may be examine 1) lung pleura (e.g., for nodules, ILD, and opacities), 2) spine (e.g., for cancer and degenerative disease), 3) ribs (e.g., for cancer, fracture, and abnormality), 4) bones (e.g., for cancer, fracture, and degenerative disease), 5) lymph stations (e.g., for cancer and disease), and 6) vasculature (e.g., for aorta dilatation, . . . ). This is a time-consuming process.

There are artificial intelligence (AI) solutions to automatically detect a small subset of findings (e.g., lung nodules in CT, and rib fractures in X-ray). However, the radiologist still has to review the whole case, including the areas where the AI system had findings (e.g., the radiologist still needs to examine the pleura for signs of airspace opacities due to infections even though a nodule detector examined the same area).

SUMMARY

By way of introduction, the preferred embodiments described below include methods, systems, instructions, and computer readable media for supporting reading for radiologists. AI identifies normal anatomy or parts of the patient represented in a medical image. Those parts are then altered, such as redacted, to indicate that no review of that part is needed. The reading presents medical images for review with one or more parts identified as not needing review (e.g., by being missing through redaction).

In a first aspect, a method is provided for artificial intelligence supported reading in a medical system. A medical image representing a patient is obtained. A first artificial intelligence examination of the medical image determines that a first anatomical part of the patient is normal. The first anatomical part of the patient is redacted from the medical image. During a reading by a radiologist, the medical image is displayed with the first anatomical part redacted.

In one embodiment, the medical image is a three-dimensional representation. Multiple two-dimensional images of the three-dimensional representation are displayed. At least two of the two-dimensional images have the first anatomical part redacted.

In another embodiment, an organ, as the first anatomical part, is determined to be normal.

According to an embodiment, the first artificial intelligence determines that a defect or disease is not in the medical image. A lack of the defect or disease indicates the anatomical part as normal. More than one artificial intelligence may be applied. For example, the first artificial intelligence was trained to detect the defect or disease for the first anatomical part. A second artificial intelligence was trained to detect a different defect or disease for the first anatomical part. The first anatomical part is determined as normal only when both the first and second artificial intelligences fail to detect the defect or disease and the different defect or disease.

In yet another embodiment, the normality determination is classifying the first anatomical part as normal.

As another embodiment, redacting includes masking the first anatomical part as a blank region in the medical image. Redacting may include altering the first anatomical part in the medical image.

In one embodiment, a second artificial intelligence detects a plurality of parts of the patient represented in the medical image. The plurality of parts including the first anatomical part and a second anatomical part. A third artificial intelligence examination of the medical image determines that the second anatomical part of the patient is normal. Redacting includes redacting both the first and the second anatomical parts from the medical image.

As yet another embodiment, the first anatomical part is segmented. The determination of normality is based on input of the first anatomical part as segmented to the first artificial intelligence.

In a second aspect, a method is provided for supported reading in a medical system. A machine-learned detector detects different anatomies represented in scan data of a patient. Different machine-learned classifiers determine whether the different anatomies are normal. Different ones of the different machine-learned classifiers determine for respective different ones of the different anatomies. A representation of at least one of the different anatomies is altered when the at least one of the different anatomies is normal. A medical image of the representation as altered is displayed. The medical image is generated from the scan data.

In one embodiment, multiple of the different machine-learned classifiers are applied to one of the different anatomies. The multiple of the different machine-learned classifiers were trained to detect different diseases or abnormalities for the one of the different anatomies.

In another embodiment, displaying includes displaying the medical image comprises displaying as part of a radiologist reading.

As another embodiment, the different machine-learned classifiers are selected from a library of machine-learned classifiers based on the anatomies detected as being represented in the scan data. This library allows for update, such as altering the machine-learned classifiers available in the library.

According to another embodiment, altering includes redacting the representation.

In a third aspect, a medical system includes a memory configured to store a medical image of a patient and a first machine-learned normality classifier; an image processor configured to apply the first machine-learned normality classifier to a part of a patient represented in the medical image and to redact the part from the medical image when the first machine-learned normality classifier determines that the part is normal; and a display configured to display the medical image with the normal part redacted.

According to one embodiment, the memory is configured to store second and third machine-learned normality classifiers for different parts of the patient represented in the medical image. The image processor is configured to apply the second and third machine-learned normality classifiers to the different parts and to redact the different parts from the medical image when the second and third machine-learned normality classifiers determine that the different parts are normal. The display is configured to display the medical image with the normal part and normal different parts redacted.

As another embodiment, the first machine-learned normality classifier includes a classifier for a first abnormality or disease of the part. The memory is configured to store a second machine-learned normality classifier for a second abnormality or disease of the part. The image processor is configured to apply the second machine-learned normality classifier to the part and to redact the part from the medical image when the first machine-learned normality classifier and the second machine-learned normality classifier both determine that the part is normal.

In another embodiment, the memory is configured to store a machine-learned detector. The image processor is configured to apply the machine-learned detector to the medical image. The machine-learned detector is configured to detect the part. The image processor configured to select the first machine-learned normality classifier based on the detection of the part.

The present invention is defined by the following claims, and nothing in this section should be taken as a limitation on those claims. Parts of one type of claim (e.g., method or system) may be used in other types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A radiologist reading is supported by AI detecting normal anatomy. The normal areas in medical images are redacted or altered. A modular AI system identifies normal anatomical regions (e.g., lung, heart, liver, . . . ) and, in the case of classifying the region as normal, the region is altered or redacted from the image presented to the radiologist.

The approach leverages modular AI components to classify normal regions. By using the automated normal detection approach, the radiologist may skip a significant number of organs during the reading process, increasing the efficiency of the reading workflow. Efficiency in the radiologist reading workflow is improved as normal regions do not need to be examined. The reading time per case is reduced for radiologists, improving operational efficiency (especially in the final stage where rule-out of full exam will be possible). Additionally, AI modules could be added over time, further improving the efficiency of the reading workflow.

Full anatomical coverage may be provided with the AI systems. The system can be gradually augmented, continuously improving the workflow efficiency. If complete anatomy coverage is established with multiple anatomy classifiers, a rule-out of normal cases is possible, removing the exam completely from the reading workflow. This allows removal of cases deemed normal by all anatomy classifiers from the reading worklist.

Figure 1:
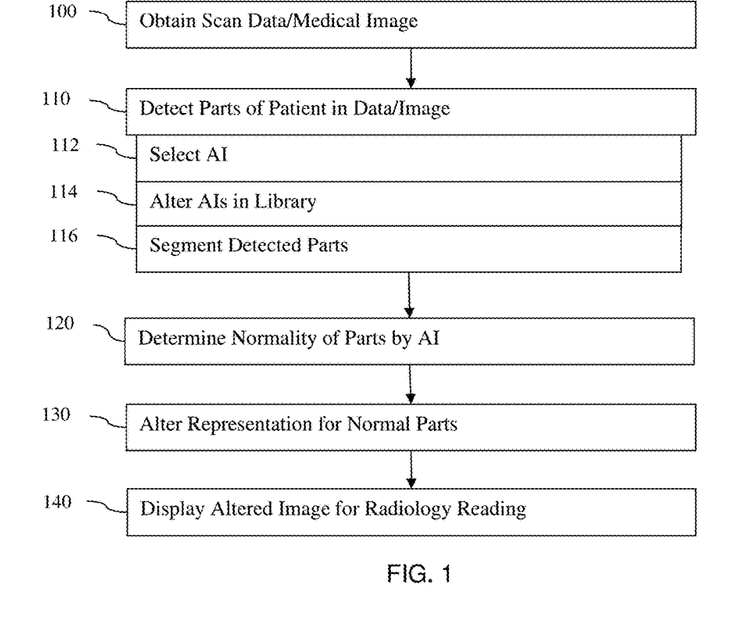
FIG. 1 is a flow chart diagram of one embodiment of a method for supporting radiology reading in a medical system.

FIG. 1 shows one embodiment of a method for supported reading in a medical system. An AI supports reading in the medical system. The AI automatically detects normal regions represented in a medical image. The normal regions are then altered so that the radiologist may ignore or more quickly review the normal regions in the image displayed for the reading. For example, the normal region or regions are redacted so that the radiologist does not spend time reviewing those regions. That part of the reading checklist may be avoided.

Figure 2:
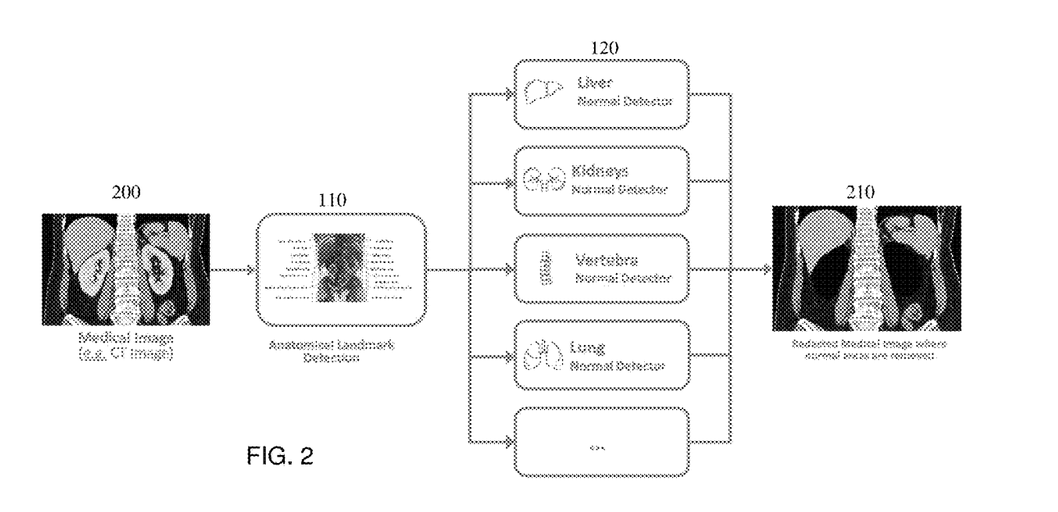
FIG. 2 illustrates use of AI for altering an image to assist reading.

FIG. 2 illustrates an example of model or portion of the method of FIG. 1. FIGS. 1 and 2 are discussed together below.

Figure 3:
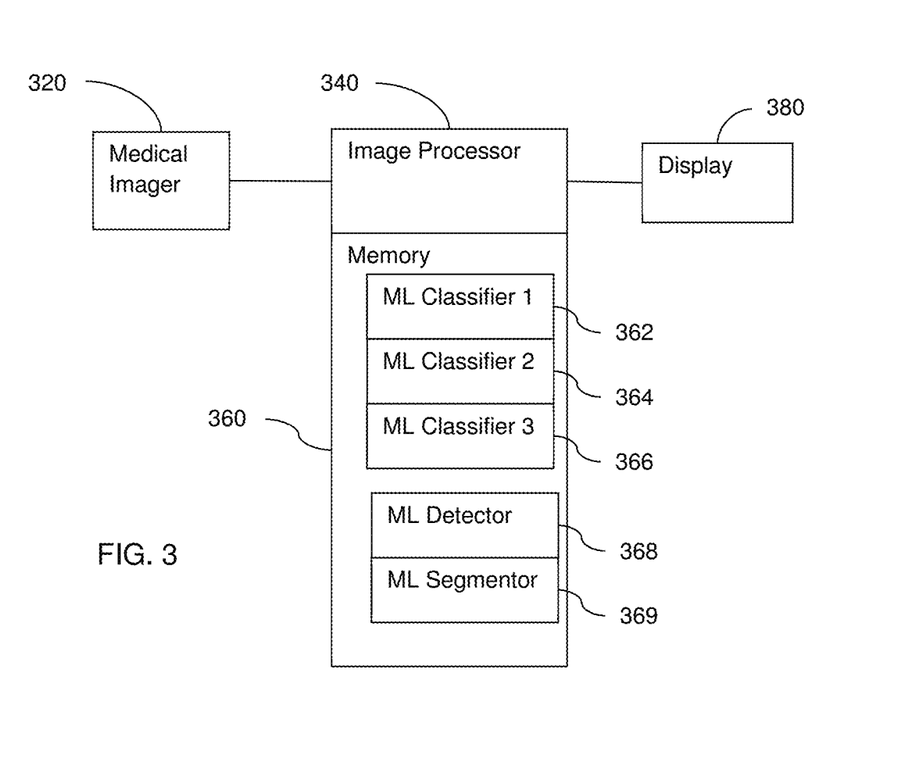
FIG. 3 is a block diagram of one embodiment of a system for machine-learned model support of radiology reading.

The method is implemented by the system of FIG. 3 or another system. For example, the method is implemented in a medical system. The medical system has access to medical information, such as patient information, so may be a workstation in a hospital, a medical scanner, or a physician's computer. The medical system is a computer, server, medical imager, or another processor. A medical imager scans the patient, or a computer accesses a picture archiving and communications system (PACS) or other storage of scan data or images in act 100. An image processor (e.g., processor of the medical imager, other processor, server, or computer) detects in act 110, determines in act 120, and alters in act 130. A same or different device (e.g., server, computer or processor) may perform acts 110, 120, and 130. A display device displays in act 140. Different devices may be used for one or more of the acts.

Additional, different, or fewer acts may be provided. For example, act 110 is not performed. As another example, any one, more, or all of acts 112, 114, and 116 are not performed. Acts for scanning, marking the image during the reading, navigating images in the reading, and/or creating the radiology report may be provided. As another example, the output is to a memory (e.g., medical record) and/or computer network rather than a display in act 140.

The acts are performed in the order shown (e.g., top to bottom or numerical) or other orders. For example, act 114 may be applied before act 112. As another example, act 116 may be performed simultaneously with acts 110 and/or act 120, such as where one AI detects a part, segments as part of the detection, and classifies as part of the detection.

In act 100, an image processor obtains a medical image 200 representing a patient. The medical image 200 is obtained by scanning with a medical imager or scanner. Alternatively, the medical image 200 is obtained by access to a memory and/or transfer over a computer network.

The medical image 200 is a computed tomography (CT), magnetic resonance (MR), ultrasound, x-ray, photoacoustic tomography, optical, magnetic particle imaging, optical coherence tomography, nuclear medicine (e.g., single photon emission computed tomography (SPECT) or positron emission tomography (PET)), or another medical image representing an interior and/or exterior of the patient.

The medical image 200 represents a plane or a volume. The patient is scanned by transmission and reception or by just reception (e.g., PET or SPECT). The scanning results in scan data representing a two or three-dimensional region of the patient. The scan data is used to generate a medical image representing the patient. Format conversion, filtering, reconstruction, rendering, mapping, and/or another process are applied to convert the scan data into a medical image 200. The medical image 200 may be scan data prior to processing. The medical image 200 represents a spatial distribution of measurements from the patient. The spatial distribution may be in one, two, or three dimensions. The medical image 200 may be a grayscale or color image displayed on or for display on a display screen or may be scalar values prior to mapping to display values. The medical image 200 is scan data formatted for display, and scan data is a medical image 200 in the scan format or prior to formatting for display.

For a medical image representing a volume, the medical image 200 may be formatted as voxels and/or as a plurality of two-dimensional slices. FIG. 2 shows the medical image 200 as one slice from a CT scan representing a volume. The medical image 200 may be a single slice or may be multiple slices, where each slice may be presented separately.

In act 110, an image processor detects one or more parts of the patient represented in the medical image 200. The medical image 200 may represent all of the patient or a region less than all of the patient. For example, the medical image 200 of FIG. 2 represents a torso region of the patient. Within the represented region are various anatomical parts, such as the liver, kidneys, vertebrae, lungs, and other parts.

The imaging ordered may indicate one or more parts (e.g., chest CT will show lungs and vertebrae) likely to be included. Based on the order, the image processor attempts to detect certain anatomical parts. Alternatively, the image processor attempts to detect various anatomical parts regardless of the ordered imaging, such as attempting to detect the brain as well as the lungs and vertebrae.

The image processor detects by application of an AI. The AI was trained to detect a particular part or parts, so a collection of AIs may be used to detect different or all the parts. Alternatively, the AI was trained to detect any parts in the medical image (e.g., one AI detecting the liver, kidneys, vertebrae, lung, and other parts). In either case, different or a plurality of anatomical parts of the patient are detected in the medical image 200.

The AI is a machine-learned model. Any machine-learned model may be used, such as a neural network, support vector machine, or Bayesian system. In one embodiment, deep learning is used to train a neural network, such as a convolutional neural network or a fully connected neural network. Example architectures for the neural network for detection and/or segmentation may be a U-Net, encoder-decoder, or image-to-image network. As another example, the machine-learned model for detection uses a deep reinforcement learned network with a trained agent to search through the medical image 200 to identify that a given anatomical part or parts is located in the image 200. Example architectures for classification may include a fully convolutional neural network to identify candidate parts and label the candidates with a greatest or sufficient probability. Another example is a hierarchal network where one part identifies candidates, such as by patch input to a neural network, and another part labels or classifies the candidates, such as by a neural network.

For machine-learned models, the architecture is defined. The defined architecture includes one or more input channels and one or more output channels. Training data is gathered, such as from past patients, clinical studies, and/or curated collections. Expert review and/or simulation may be used to create the training data. The training data includes tens, hundreds, thousands, or more examples of the input and output. The sample outputs are ground truth for training. Some objective criteria (e.g., measure of quality) may be used for the output so that ground truth is not needed in the training data. Multi-task learning may be used so that the output benefits from errors determined for other more widely available data.

The architecture includes learnable parameters. An optimization, such as Adam or gradient decent, is performed to learn the values of the learnable parameters that result in the most accurate output given the input. A loss or error between the output and the ground truth and/or objective criteria is used in back-propagation as part of the optimization to determine the values for the learnable parameters. Once trained, the architecture with the values of the learned parameters are applied to previously unseen data for patients.

For act 110, the AI was trained to detect one or more anatomical parts represented in the medical image 200. After training, the machine-learned detector is applied using the learned values of the parameters and the architecture. The image processor inputs the medical image 200 or patches from the medical image 200 to the machine-learned detector, which outputs landmarks of the part, that the anatomical part is in the medical image 200, and/or a segmentation of the anatomical part in the medical image 200. Different anatomies represented in the scan data (e.g., medical image 200) of the patient are identified or detected. The medical image 200 is analyzed automatically by detecting anatomical landmarks, such as using AI based on Deep Reinforcement Learning.

The detection indicates which parts are in the medical image 200. This allows the medical system to then determine which of the parts are normal. The detection provides a list of one or more (e.g., all) anatomical parts represented in a given medical image 200.

In act 112, the image processor selects AIs to determine normalcy. An array of AI modules may be used to determine which parts are normal. Alternatively, one AI determines whether multiple or different parts are normal. Different machine-learned classifiers are selected from a library of machine-learned classifiers based on the anatomies detected as being represented in the scan data. For example, an AI for classification of normalcy of lungs is selected, and an AI for classification of normalcy of the liver is selected. Alternatively, one machine-learned classifier is selected.

In act 114, the AIs available for selection are changed. As new AIs for different parts become available, those AIs may be added to the library. As a better (e.g., fewer false positives) AI for a given part becomes available, the previous AI for that part may be replaced. The library of AIs is altered to improve performance of normalcy detection. As the approach leverages modular AI components to classify normal regions, the medical system can be gradually augmented, continuously improving the workflow efficiency.

In act 116, the image processor segments the detected anatomical parts. A boundary, mask, and/or locations of the anatomical part are identified. The detection itself may provide the segmentation. Alternatively, a separate AI is applied to segment. For example, the detection identifies one or more landmarks indicative of the part. A separate segmentation is then applied to identify the boundary or all locations of the part represented in the medical image 200.

The image processor applies the AI (machine-learned detector) for detection or another AI to segment. Different AIs may be provided for segmenting different anatomical parts. In one embodiment, one or more machine-learned segmentors are applied to segment the different anatomical parts. Different segmentation AIs may have the same or different architecture. In one embodiment, an image-to-image deep neural network is used to segment a part, such as the lungs. Other trained neural networks are used to segment other parts, such as the liver, kidneys, bones, vertebrae, and others.

In act 120, the image processor determines whether the different detected anatomies are normal. The determination of normalcy may be through determining that the anatomical part is not abnormal or determining that the anatomical part is normal. Where the part is normal, then review by the radiologist may be limited. Where the part is not normal, then the radiologist is to review.

The determination of normalcy uses one or more machine-learned classifiers. The same or different AI is applied to classify the different parts as normal or not. Different AIs may be provided for respective different parts (e.g., machine-learned classifier for lungs determines for lungs, and a machine-learned classifier for kidneys determines for the kidneys). The different AIs were trained to detect for different parts. The segmented part is input as a whole or in patches to the machine-learned classifier, which then outputs a class label, such as normal or abnormal.

The image processor applies the selected AI for each detected anatomical part. The AI uses input data to generate an output. The input data is the segmentation or region of the medical image 200 representing the part with or without other context (e.g., other regions of the medical image 200 and/or patient clinical data). In one embodiment, the image data is input. Alternatively, features derived from the image data for the part are input. Other data may be input, such as other patient data (e.g., test results, family history, and/or patient characteristics).

In response to input of the input, the AI outputs the classification. For example, the lung AI outputs that the lungs are normal. Some parts may be determined as normal and other determined as abnormal. All parts may be determined as normal.

In one embodiment, more than one AI is applied for an anatomical part. For example, different machine-learned classifiers are trained to detect different abnormalities and/or diseases. By applying multiple AIs, the image processor examines the part as represented in the medical image 200 for the different abnormalities and/or diseases. If none of the AIs detect any abnormalities and/or diseases, the part is determined to be normal. If any abnormality and/or disease is detected, then the part is determined to be abnormal. Alternatively, one AI is applied to detect multiple or all abnormalities or diseases. In yet another alternative, the AI was trained to identify a normal part, so the determination is whether the part is normal without specific determination for a given disease and/or abnormality.

The AI examines the medical image 200, such as the segmented part, to determine whether that anatomical part is normal. The image processor classifies the anatomical part as normal or not, such as determining that an organ is normal (e.g., lungs are normal). There is no defect or disease represented in the medical image 200 for that anatomical part. A view that represents normal or a view that shows no defect or diseases is labeled normal by the AI.

In the example of FIG. 2, one or more machine-learned classifiers indicate that the kidneys are normal. Other machine-learned classifiers determine that there may be one or more defects or diseases represented in the liver, vertebrae, and lungs. Other parts are not detected and/or are not analyzed for normalcy, so remain in the medical image 200.

In act 130, the image processor alters a representation of at least one of the different anatomies when the at least one of the different anatomies is normal. For each anatomical part classified as normal, the medical image 200 is altered. The alteration indicates to the radiologist that less or no review time is needed for that part.

The alteration is highlighting, coloring, reducing resolution, and/or graying out. The locations for the normal anatomical part are indicated as normal through alteration. For example, the segmented border and/or locations for the kidneys are colored.

In one embodiment, the alteration is to redact the representation of the normal anatomical organ. The scan data represented in the medical image 200 is removed or masked. FIG. 2 shows an example. The kidneys are automatically determined to be normal by the AI. The kidneys in the medical image 200 are redacted from the medical image 200, resulting in the altered medical image 210. The normal areas are removed, such as redacting the anatomical part of the patient from the medical image 200. The normal anatomical part is masked as a blank (e.g., black or white) region in the medical image 210. If the anatomy is deemed normal, the anatomical region is redacted from the scan.

Where multiple anatomical parts are determined to be normal, then the multiple anatomical parts are altered (e.g., redacted). Where none of the anatomical parts are determined to be normal, then medical image 200 is not altered.

In alternative embodiments, portions of anatomical parts are redacted. A portion of the anatomical part may be determined to be normal, while another portion is not. The normal portion of the anatomical part is redacted or altered. The medical image 200 may be altered to indicate which parts have been analyzed and/or which have not been analyzed by AI.

In act 140, the image processor generates and passes an altered medical image 210 to a display device. The altered medical image 210 is presented for viewing by a radiologist. Multiple slices may be presented, with each having been altered to indicate normal or abnormal regions.

The altered medical image 210 is displayed as part of a radiologist reading. The radiologist is presented with images from a scan for a given patient. For a three-dimensional scan or representation, the radiologist is presented with multiple two-dimensional images representing different parts of the scanned volume (e.g., different slices). The radiologist reviews each slice or image. Each of the images is altered to remove or indicate normal anatomy.

The radiologist navigates through the images. Each of the images is altered to indicate (e.g., redact or remove) normal anatomy, so that any anatomy with abnormal (e.g., possible defect and/or disease) presentation is output for review. The normal regions are not output or are displayed in a way indicating less need or no need for review. During the reading to generate a radiology report, the radiologist benefits from the automated determination of normalcy. Less time may be spent reviewing due to the list of anatomical parts to be reviewed being less.

FIG. 3 shows a block diagram of one embodiment of a medial system for supporting radiologist reading. Normal anatomy is automatically determined so that the patient images presented to the radiologist focus on the non-normal anatomy. The system implements the model of FIG. 2, the method of FIG. 1, or a different model or method.

The system includes one or more medical imagers 320, an image processor 340, a memory 360 (e.g., a medical records database), and a display 380. Additional, different, or fewer components may be provided. For example, a user interface or input device is provided on the medical imager 320 and/or for the image processor 340. In another example, a network or network connection is provided, such as for networking different components (e.g., medical imager 320 with the image processor 340 and/or the image processor 340 with the memory 360). As another example, the medical imager 320 is not provided, such as where the scan data for a patient is stored in the memory 360 or accessible to the image processor 340.

The memory 360, image processor 340, and/or display 380 are part of a server, workstation, or computer. In one embodiment, the memory 360, image processor 340, and/or display 380 are part of the medical imager 320. The memory 360 may be part of a separate computer from the image processor 340, such as being in a cloud hosted electronic health record, electronic medical records system, or PACS.

The medical imager 320 is a magnetic resonance (MR), computed tomography (CT), x-ray, ultrasound, nuclear medicine (e.g., PET or SPECT), or another medical scanner. In other embodiments, the medical imager 320 is a multi-modality device, such as a combination of nuclear medicine and x-ray or CT.

The medical imager 320 is configured to scan a patient. The same imager 320 may be used to scan different patients at different times. Other imagers 320 may be used to scan other patients. The medical imager 320 is configured to output scan data to the image processor 340. The scan data is data resulting from the scan at any stage of processing. For example, data without reconstruction is provided. For CT, the data may be detector measurements for a plurality of projections without reconstruction into values for specific spatial locations. For MR, the data may be k-space data prior to Fourier transform to determine values for specific spatial locations. For nuclear imaging, the data may be line-of-response values prior to tomography to assign specific spatial locations. As another example, data after reconstruction is provided. Filtering, detection, scan conversion, and/or other image processing may or may not be applied to the data for communication to the image processor 340. The medical imager 320 provides image data (e.g., scan data) as data resulting from scanning with any amount of processing towards generating an image on the display 380. The image data may be formatted for display, such as RGB values, or may be in a scan format (e.g., scalar values).

The memory 360 is a random-access memory, system memory, cache memory, hard drive, optical media, magnetic media, flash drive, buffer, database, combinations thereof, or another now known or later developed memory device for storing patient information (e.g., images) and/or a library of available machine-learned models. The memory 360 is part of the computer associated with the image processor 340 or the medical imager 320 or is a separate or remote database for access over a computer network.

The memory 360 stores a library of machine-learned models (e.g., stores the architecture and learned values). The machine-learned models of the library are for different or the same clinical tasks. More than one machine-learned model may be available for a given task and type of imaging. FIG. 3 shows three machine-learned classifiers 362, 364, 366 for automatic normalcy determination. Multiple classifiers 362, 364, 366 are for multiple different anatomical parts, but two or more classifiers 362, 364, 366 may be for normalcy classification for a same anatomical part. FIG. 3 also shows a machine-learned detector 368 for detecting anatomical parts. One machine-learned detector 368 detects different anatomical parts. In other embodiments, the memory 360 stores different machine-learned detectors 368 for detecting different anatomical parts. FIG. 3 also shows a machine-learned segmentor 369 for segmenting anatomical parts. In other embodiments, the memory 360 stores different machine-learned segmentors 369 for segmenting different anatomical parts. This library 36 of AI offerings includes multiple options to be applied or used for a given patient.

The memory 360 may store patient information (e.g., medical image data from the medical imager 320 or another imager and/or other patient data). The memory 360 may include a computerized medical record for the patient. Some or all of the patient information may be provided by transfer or access to a device other than the memory 360.

The memory 360 or other memory is alternatively or additionally a non-transitory computer readable storage medium storing data representing instructions executable by the programmed processor 340 and/or medical imager 320. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, tensor processing unit (TPU), neural processing unit, AI accelerator, or system.

The image processor 340 is a general processor, control processor, digital signal processor, application specific integrated circuit, field programmable gate array, AI processor, tensor processor, graphics processing unit, or another hardware processor for applying machine-learned models and altering images for presentation as part of a reading by a radiologist. In one embodiment, the image processor 340 is part of a computer, workstation, server, or other device configured to select and apply a machine-learned model. The image processor 340 may be a network of computing devices, such as multiple computers or servers.

The image processor 340 is configured by software, hardware, and/or firmware. The image processor 340 or another processor configures the memory 360 by formatting and/or storage.

The image processor 340 is configured to apply one or more machine-learned detectors 368 to the medical image. Based on the previous machine learning, the machine-learned detectors 368 are configured to detect one or more parts.

The image processor 340 is configured to select machine-learned normality classifiers 362, 364, 366 based on the detection of the parts. One or more classifiers 362, 364, 366 are selected for each of the detected parts.

The image processor 340 is configured to apply the selected machine-learned classifiers 362, 364, 366. For each detected part of the patient represented in a medical image, one or more classifiers 362, 364, 366 are applied to determine whether the part is normal or not. Different classifiers 362, 364, 366 may be applied to different parts. Multiple classifiers 362, 364, 366 may be applied to the same part, such as to determine whether different defects and/or diseases are detectable within that part. The part is normal only where all of the classifiers 362, 364, 366 for that part indicate normal (e.g., lack of different defects and/or diseases).

The image processor 340 is configured to redact any normal part from the medical image. Other alteration may be used. When the machine-learned normality classifier 362 or classifiers 362, 364, 366 determine that the part is normal, then that part is removed from the medical image. Different parts may be redacted from the medical image when the machine-learned normality classifiers 362, 364, 366 determine that the different parts are normal. Possibly abnormal, regions not associated with a detected anatomical part, and/or remaining regions remain in the medical image.

The display 380 is a monitor, LCD, projector, plasma display, CRT, printer, or another now known or later developed device for displaying an altered medical image during a reading. By applying the machine-learned models, the output medical image focuses the radiologist on possible abnormal anatomy. The display 380 displays the altered medical image, such as the medical image 210 of FIG. 2 with the redacted kidneys. The normal part or parts are redacted. Some normal parts may remain, such as where the part was not detected or analyzed.

The display 380 receives the altered medical image from the image processor 340, medical imager 320, or memory 360. The image processor 340 formats the data for display (e.g., mapping to RGB values) and stores the image in a buffer or display plane, configuring the display 380. The display 380 uses the image in the buffer to generate the altered medical image for viewing. The display 380 is at the medical imager 320, the image processor 340, a physician's computer, or another location.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for artificial intelligence supported reading in a medical system, the method comprising:
   obtaining, by a medical imager, a medical image representing a patient, wherein a portion of the medical image comprises at least a first anatomical part of the patient;
   determining, by a first artificial intelligence examination of the medical image, that the first anatomical part of the patient is normal;
   redacting the portion of the medical image comprising the first anatomical part of the patient from the medical image; and
   displaying, during a reading by a radiologist, the medical image with the first anatomical part redacted wherein a remaining portion of the medical image is unredacted.

2. The method of claim 1 wherein obtaining the medical image comprises obtaining the medical image as a three-dimensional representation as the medical image, wherein displaying during the reading comprises displaying of multiple two-dimensional images of the three-dimensional representation, at least two of the two-dimensional images having the first anatomical part redacted.

3. The method of claim 1 wherein determining comprises determining that an organ as the first anatomical part is normal.

4. The method of claim 1 wherein determining comprises determining, by the first artificial intelligence, that a defect or disease is not in the medical image, a lack of the defect or disease indicating the normal.

5. The method of claim 4 wherein the first artificial intelligence was trained to detect the defect or disease for the first anatomical part, and a second artificial intelligence was trained to detect a different defect or disease for the first anatomical part, and wherein the first anatomical part is determined as normal only when both the first and second artificial intelligences fail to detect the defect or disease and the different defect or disease.

6. The method of claim 1 wherein determining comprises classifying the first anatomical part as normal.

7. The method of claim 1 wherein redacting comprises masking the first anatomical part as a blank region in the medical image.

8. The method of claim 1 wherein redacting comprises altering the first anatomical part in the medical image.

9. The method of claim 1 further comprising:
   detecting, by a second artificial intelligence, a plurality of parts of the patient represented in the medical image, the plurality of parts including the first anatomical part and a second anatomical part; and
   determining, by a third artificial intelligence examination of the medical image, that the second anatomical part of the patient is normal;
   wherein redacting comprises redacting both the first and the second anatomical parts from the medical image.

10. The method of claim 1 further comprising segmenting the first anatomical part, and wherein determining comprises determining based on input of the first anatomical part as segmented to the first artificial intelligence.

11. A method for supported reading in a medical system, the method comprising:
   detecting, by a machine-learned detector, different anatomies represented in scan data of a patient;
   determining, by different machine-learned classifiers, whether the different anatomies are normal, different ones of the different machine-learned classifiers determining for respective different ones of the different anatomies;
   altering a representation of at least one of the different anatomies when the at least one of the different anatomies is normal; and
   displaying a medical image of the representation as altered, the medical image being generated from the scan data.

12. The method of claim 11 wherein multiple of the different machine-learned classifiers are applied to one of the different anatomies, the multiple of the different machine-learned classifiers having been trained to detect different diseases or abnormalities for the one of the different anatomies.

13. The method of claim 11 wherein displaying comprises displaying the medical image comprises displaying as part of a radiologist reading.

14. The method of claim 11 wherein the different machine-learned classifiers are selected from a library of machine-learned classifiers based on the anatomies detected as being represented in the scan data.

15. The method of claim 14 further comprising: altering the machine-learned classifiers available in the library.

16. The method of claim 11 wherein altering comprises redacting the representation.

17. A medical system comprising:
- a memory configured to store a medical image of a patient and a first machine-learned normality classifier wherein the memory is configured to store a second machine-learned normality classifier and a third machine-learned normality classifier for different parts of the patient represented in the medical image;
- an image processor configured to apply the first machine-learned normality classifier to a part of a patient represented in the medical image and to redact the part from the medical image when the first machine-learned normality classifier determines that the part is normal, wherein the image processor is further configured to apply the second and third machine-learned normality classifiers to the different parts and to redact the different parts from the medical image when the second and third machine-learned normality classifiers determine that the different parts are normal; and
- a display configured to display the medical image with the normal part and normal different parts redacted.

18. The medical system of claim 17 wherein the first machine-learned normality classifier comprises a classifier for a first abnormality or disease of the part, wherein the memory is configured to store a second machine-learned normality classifier for a second abnormality or disease of the part, wherein the image processor is configured to apply the second machine-learned normality classifier to the part and to redact the part from the medical image when the first machine-learned normality classifier and the second machine-learned normality classifier both determine that the part is normal.

19. The medical system of claim 17 wherein the memory is configured to store a machine-learned detector, wherein the image processor is configured to apply the machine-learned detector to the medical image, the machine-learned detector configured to detect the part, the image processor configured to select the first machine-learned normality classifier based on the detection of the part.

* * * * *